United States Patent
Zhang et al.

(10) Patent No.: US 7,262,181 B2
(45) Date of Patent: Aug. 28, 2007

(54) WATER SOLUBLE CELLULOSE ETHERIFIED DERIVATIVES STYPTIC MATERIALS

(75) Inventors: Mei Zhang, Beijing (CN); Jinyu Zhang, Beijing (CN); Xia Song, Beijing (CN)

(73) Assignee: Beijing Textile Research Institute, Beijing (CN)

( * ) Notice: Subject to any disclaimer, the term of this patent is extended or adjusted under 35 U.S.C. 154(b) by 0 days.

(21) Appl. No.: 10/476,559

(22) PCT Filed: Apr. 30, 2001

(86) PCT No.: PCT/CN01/00681

§ 371 (c)(1),
(2), (4) Date: Jun. 6, 2005

(87) PCT Pub. No.: WO02/087643

PCT Pub. Date: Nov. 7, 2002

(65) Prior Publication Data

US 2006/0014721 A1    Jan. 19, 2006

(51) Int. Cl.
*A61K 31/717* (2006.01)
*C08B 11/12* (2006.01)

(52) U.S. Cl. .................. 514/57; 536/1.11; 536/56; 536/84; 536/91; 536/96; 536/98

(58) Field of Classification Search .................. 514/57; 536/1.11, 56, 84, 91, 96, 98
See application file for complete search history.

(56) References Cited

U.S. PATENT DOCUMENTS

| | | | | |
|---|---|---|---|---|
| 2,682,535 A | * | 6/1954 | Broderick | 536/85 |
| 3,085,087 A | * | 4/1963 | Henry et al. | 536/98 |
| 4,289,824 A | * | 9/1981 | Smith | 428/300.1 |

FOREIGN PATENT DOCUMENTS

| | | | |
|---|---|---|---|
| EP | 0 815 881 | | 1/1998 |
| GB | 2314840 | * | 1/1998 |
| JP | 63220876 | | 9/1988 |
| JP | 6233809 | | 8/1994 |

OTHER PUBLICATIONS

Timell, T.E. et al, Can. J. Chem. 1960, 38, 1191-98.*

* cited by examiner

*Primary Examiner*—Shaojia Anna Jiang
*Assistant Examiner*—Ganapathy Krishnan
(74) *Attorney, Agent, or Firm*—Oblon, Spivak, McClelland, Maier & Neustadt, P.C.

(57) ABSTRACT

The present invention relates to hemostatic materials made of water-soluble cellulose ether derivatives, such as methylcellulose, ethylcellulose, hydroxyethylcellulose, and pharmaceutically acceptable salts of carboxymethylcellulose, especially to hemostatic materials made of water-soluble cellulose ether derivatives capable of being absorbed in live body. The present invention also relates to the use of water-soluble cellulose hemostatic materials for the preparation of internal and external hemostatic articles and pharmaceutical compositions, and hemostatic articles and pharmaceutical compositions thereof.

22 Claims, No Drawings

WATER SOLUBLE CELLULOSE ETHERIFIED DERIVATIVES STYPTIC MATERIALS

FIELD OF THE INVENTION

The present invention relates to materials made of water-soluble cellulose ether derivatives, especially to materials made of water-soluble cellulose ether derivatives capable of being absorbed in live body, such as fibers, webs, non-woven fabrics, powders and colloids. The present invention also relates to the use of the materials made of water-soluble cellulose ether derivatives in products for medical treatment including hemostatic, wound protection, prevention of operation-adhesion, colorful bandages for human body and skin care applications, products for package and woven products, as well as articles such as sheet articles, columnar articles, plug articles, colloidal articles, film articles, sponge articles, aerosols, band aids, transfusion bandage, first-aid kit, operation kit, color bandage, top sheet, water-soluble packaging material, water-soluble decrement mixed yarn, cloth and the like.

BACKGROUND OF THE INVENTION

Traditional hemostatic materials, such as gelatin sponges, microcrystalline collagens and collagen proteins, are prepared from skins and bones of animals, which easily result in antigen reaction of tissues. Additionally, these materials have large stimulation to the tissues, and after an operation, cicatricle tissues proliferate and adhesion easily occurs. Meanwhile, the materials are poor in stability and inconvenient in storage and use. The use of animal medical materials is thus restricted in the world. Natural vegetable hemostatic materials are being used to replace animal hemostatic materials.

Recently, reports and patents that relate to the use of oxidized cellulose, cellulose esters and ethers products as medically hemostatic materials have been found, however, most of the materials are water-insoluble.

U.S. Pat. No. 2,914,444 entitled with Cellulose hemostatic composition discloses a series of cellulose derivatives useful for hemostatic agents alone or in combination with each other, including cellulose sulfonic acid ester (substituting degree 1-3) or metal(sodium, potassium, calcium, magnesium, aluminum) salts thereof, cellulose glycolic acid ether (substituting degree 0.5-3.0) or metal salts thereof. U.S. Pat. No. 2,914,444 emphasizes that the product can be used only after being made water-insoluble. U.S. Pat. No. 3,122,479 entitled with Hemostatic surgical dressings discloses methods for making the materials of the above-mentioned invention into water-insoluble sponges, slightly water-soluble elastic films and water-insoluble oxidized cellulose compressed cottons. U.S. Pat. No. 2,764,159 entitled with Absorbable products discloses a method for making absorbable fiber filaments, sponges, films and powders comprising dissolving a cellulose glycolic acid ether salt, spinning, and then making it into an insoluble acid product by using an inorganic acid. According to U.S. Pat. No. 2,764,159, the free acid cellulose ethers have a viscosity less than 17.4 seconds in a 0.5N NaOH aqueous solution, preferably, 5.7-12.0 seconds; and a degree of substitution of 0.5-0.7, and at most 2.0. Soluble cellulose ether salts are used as starting materials in the first step for preparing the product; even though the final product contains a part of salt groups, it meantime must contain a certain proportion of free carboxylic acid groups, i.e., about 50% carboxylic acid groups remain un-neutralized, with a pH value of 2-5.5 to ensure the product insoluble or slightly soluble. Chinese patent application No. 97117113 entitled with Bio-absorbable medical materials from oxidized polysaccharides discloses the preparation of absorbable medical materials by using (methyl, ethyl, or carboxymethyl) cellulose ethers and other polysaccharides as starting materials and carrying out post-oxidation treatment. After being oxidized, except that methylcellulose ether is still soluble, other ethers products all become insoluble. Moreover, the cellulose derivatives of the patent application are used to prevent operation adhesion, and their hemostatic activity is not mentioned therein.

Chinese patent No. 1035803C describes a method for manufacturing water-soluble hemostatic fabrics. The method does not control the degree of substitution and the degree of polymerization of the product. However, the present applicant has found that the degree of substitution and the degree of polymerization of a product has a direct effect on its hemostatic effect. The patent states that the product of formula II can be absorbed in vivo, whereas the degree of polymerization of the product is disclosed as 800-1,200 (twice of 400-600). Thus the product will have a molecular weight greater than 120,000 and it will be difficult for the product to enter into circulating system via vascellum wall for excretion (See, S. D. Bruck, Properties of Biomaterial in the Physiological Environment, and D. F. Williams, Fundamental Aspects of Biocompatibility). In addition, as described hereinafter, the material having a too large degree of polymerization forms gel after being implanted in the body, has a large swelling volume, and produces oppression to peripheral tissues, which will cause inflammatory reaction, fiber proliferation, and formation of liquefied cavity.

SUMMARY OF THE INVENTION

Therefore, the present invention aims to provide the use of etherified celluloses having improved water solubility and biologic absorbency in medical and treatment products.

The present invention further aims to provide an etherified cellulose derivative having improved water solubility and biologic absorbency.

According to the first embodiment of the invention, the present invention provides the use of an etherified cellulose derivative selected from a group consisting of water-soluble methylcellulose, ethylcellulose, hydroxyethylcellulose and salts of carboxymethylcellulose, which has a degree of substitution of 0.4-2.6, an average degree of polymerization of 100-1500 and a carbonyl content above 0 and below 2%, in the preparation of medical and treatment products, such as products used for hemostasis, protection of wounded area, preventing operation adhesion and the like.

According to the second embodiment of the invention, the present invention provides a water-soluble etherified cellulose having an average degree of polymerization of 100-400 and a carbonyl content not higher than 2%, selected from a group consisting of methylcellulose, ethylcellulose, hydroxymethylcellulose and salts of carboxymethyl cellulose having a degree of substitution of 0.4-0.9.

According to the third embodiment of the invention, the present invention provides various articles made of the water-soluble cellulose ether derivatives as described above, such as, for example, woven products, non-woven cloths, sponges, films, powders, colloids, columns, plugs, aerosols, band-aids, transfusion bandages, first-aid kits, operation kits, colorful bandages for human body and skin care masks, water-soluble packaging materials, water-soluble decrement mixed yarn, cloths and the like.

According to the fourth embodiment of the invention, the present invention provides a process for preparing the water-soluble cellulose ether derivatives as described above.

Particularly, the present invention provides a salt of water-soluble carboxymethylcellulose having an average degree of polymerization of 100-400, a degree of substitution of 0.4-0.9, and a carbonyl content not higher than 2%, use thereof and articles thereform.

DETAILED DESCRIPTION OF THE INVENTION

The inventor has carried out a lot of basic experiments, animal experiments and clinic comparative experiments to test various properties of water-soluble and water-insoluble etherified cellulose materials. The results show that water-soluble etherified cellulose materials exhibit better property than water-insoluble hemostatic materials; those water-soluble etherified cellulose materials having a suitable degree of polymerization, a certain carbonyl amount and a certain degree of substitution show rapid absorption rate and small reaction of tissue; moreover, they can prevent operation adhesion and have notable effect on the patients suffering from blood coagulation disorders.

Furthermore, the present inventor found that the degrees of substitution and of polymerization of the water-soluble etherified cellulose material are easily controlled within the specific range when the carbonyl amount thereof is from 0% to 2%. Specifically, a medical or care material of improved water solubility and absorbency can be obtained if the water-soluble etherified cellulose material can meet all the following conditions: 1) the degree of polymerization equals to 100-1500; 2) the degree of substitution equals to 0.4-2.6; and 3) the carbonyl amount is not higher than 2%.

In particular, the inventor has discovered that the medical and care effect of water-soluble methylcellulose, ethylcellulose and hydroxyethylcellulose having specific degrees of polymerization and substitution and specific carbonyl amount is better than that of water-insoluble hemostatic materials. The applicant further found that the effect of salts of carboxymethylcellulose having a degree of substitution of 0.4-0.9, a degree of polymerization of 100-400 and a carbonyl amount of not higher than 2% is notably better than that of water-soluble carboxymethylcellulose salts having other degrees of substitution. Therefore, the present invention relates to these novel water-soluble celluloses.

The water solubility of etherified cellulose is directly related to its degree of substitution. In particular, water-soluble methylcellulose is generally of a degree of substitution of 1.3-2.6, preferably 1.5-2.2, more preferably 1.8-2.0. Water-soluble ethylcellulose is usually of a degree of substitution of 1.0-1.5, preferably 1.1-1.4, more preferably 1.2-1.3. Water-soluble hydroxyethylcellulose means those having a degree of substitution of 0.8-2.5, preferably 1.0-2.0, more preferably 1.5-1.8. Carboxymethylcellulose alkali salts are generally water-soluble ones having a degree of substitution of 0.4-1.2. The invention uses pharmaceutically acceptable salts of carboxymethylcellulose having a degree of substitution of 0.4-0.9, preferably 0.45-0.9, more preferably 0.5-0.85, which exhibit prominent hemostatic effect. The method for the measurement of degree of substitution is based on ASTM of U.S.A, Association of Standards of Test Materials.

As regard to carboxymethylcellulose salt, when its degree of substitution is less than 0.4, the material can only absorb water and swell, can be dissolved in dilute base, and can be incompletely dissolved in water is incomplete. When its degree of substitution is greater than 1.0, its water solubility is reduced, but it can be dissolved in polar solvent. When the alkali metal ion of carboxymethylcellulose salt is replaced by hydrogen ion, all carboxymethylcelluloses having arbitrary degree of substitution are water-insoluble. In the invention, the degree of substitution of carboxymethylcellulose sodium salt is controlled in the range of 0.4-0.9, therefore, good medical effect is obtained, and foreign body reaction of tissue is low. Other cellulose ethers have similar properties as those of carboxymethylcellulose in the range described in the invention.

The present inventor further found that the water-soluble etherified cellulose having a degree of polymerization of 100 to 400 and a certain amount of carbonyl exhibits excellent bio-absorbency. Thus the present invention relates to a water-soluble etherified cellulose selected from a group consisting of methylcelluose, ethylcellulose, hydroxymethyl-cellulose and carboxymethylcellulose salts, which has an average degree of polymerization of 100 to 400, a carbonyl amount not higher than 2% and a certain degree of substitution. The present inventor found during the experiments that it is difficult for the oxidation-etherified cellulose having a degree of polymerization greater than 400 to be absorbed in the body after implanted, thereby resulting in inflammatory reaction, fiber proliferation, and formation of liquefied cavity.

While the oxidized-etherified cellulose having a degree of polymerization of lower than 100 exhibits poor physical properties, such as hard hand feel, poor strength, too rapid dissolving speed, easy adhesion to apparatus in using, and inconvenient operation. In a range of the degree of polymerization of 100-400, water-soluble etherified cellulose materials exhibit suitable physical properties and hemostatic activity, and excellent absorption characteristics in vivo.

The present inventor also found that the water-soluble etherified cellulose having a pH value controlled in a specified range exhibits slight biologic irritation. Specifically, the water-soluble etherified cellulose having a pH value of 6 to 8 according to the present invention exhibits good solubility and slight irritation in vivo.

In the invention, the degree of polymerization of the water-soluble etherified cellulose capable of being biologically absorbed is preferably 100-350, more preferably 150-350, most preferably 150-300. The degree of polymerization is determined by "specific viscosity method".

In the invention, the carbonyl amount of the water-soluble etherified cellulose capable of being biologically absorbed is preferably 0.001-2%.

In the invention, the degree of polymerization of a etherified cellulose represents the mean number of anhydroglucose units contained in one cellulose molecule.

In this aspect, the invention preferably uses salts of water-soluble carboxymethylcellulose having a degree of polymerization of 100-400 and a carbonyl amount less than 2%.

In a particularly preferred embodiment, the invention relates to salts of water-soluble carboxymethylcellulose having a degree of substitution of 0.5-0.85, a degree of polymerization of 100-400 and a carbonyl amount below 2%.

In the invention, salts of carboxymethylcellulose mean the salts formed by the carboxylic acid contained in the above-mentioned carboxymethylcellulose and/or etherified cellulose containing a certain carbonyl amount and a physiologically acceptable cation capable of forming a water-soluble salt. The salts suitable in the present invention preferably include alkali salts, alkaline earth salts and aluminum salts, especially sodium salts, potassium salts, calcium salts, magnesium salts and aluminum salts.

Optionally, the water-soluble etherified cellulose according to the present invention can be impregnated into a mixed solution containing $Ca^{2+}$, an organic solvent such as methanol, ethanol and propanol, and water, thereby adsorbing 0.01 to 2wt % of $Ca^{2+}$ so that the hemostatic effect can be improved.

The etherified cellulose of the invention can be prepared by using the techniques, e.g. alkalization-etherification, etherification-alkalization, alkalization-etherification-alkalization or oxidation-alkalization-etherification. For example, the etherified cellulose of the invention can be prepared from natural or regenerated cellulose via the above routes. Among the routes, the alkalization-etherification process has an advantage of rapid reaction, but is poor in reaction homogeneity due to the swelling of celluloses under an alkali condition, which adversely affects the penetration of the etherified solution. The etherification-alkalization process needs a long reaction time, but is good in reaction homogeneity. The resulting cellulose material has soft hand feel, slow-dissolving, and no adhesion to an apparatus. The alkalization-etherification-alkalization process has a moderate reaction time and excellent reaction homogeneity. Those skilled in the art can determine the degree of substitution, the degree of polymerization and carbonyl content according to the methods disclosed or the methods described herein so as to obtain the cellulose materials having specified parameters of the invention. In the process of alkalization-etherification, products can be alkalized by using hydroxides of K, Na, Ca, Mg or Al, and can be etherified by using alkyl halides or alkanes containing an active hydroxy group or ether bond. In the process of oxidation-alkalization-etherification, products can be oxidized by the oxidants, such as hypochlorites, peroxides, nitrogen dioxide and nitrogen tetroxide.

For instance, the water-soluble carboxymethylcellulose salts (I type) containing no carbonyl group may be prepared by the following methods:
a) using a natural cellulose absorbent cotton, absorbent gauze, fiber, powder, non-woven cloth or sponge as raw materials;
b) putting the raw materials into a closed reactor and reacting in a 30-48% by weight of an alkali metal hydroxide (preferably NaOH) as a reaction medium, or a mixed reaction medium of $C_1$-$C_5$ lower alkanol (preferably ethanol, acetone or isopropanol and mixture thereof) and 35-45% by weight of an alkali metal hydroxide at a bath ratio 1:5-30 and a temperature of 15-30° C. for 0.5-4 hours;
c) adding alkyl halide or haloacetic acid, and 20-80% by weight of $C_1$-$C_5$ lower alkanol having a weight 1-15 times of the weight of the raw materials to the system from b) and allowing to etherify at 15-140° C. for 1-12 hours;
  Notes: the order of the above steps b) and c) can be inverted; or the reaction can be carried out by feeding in sequence half of the amount of feed of b), whole amount of feed of c), and then the other half of amount of the feed of b).
d) neutralizing the resulting product from c) to pH 6-8 with $C_1$-$C_5$ lower alkanol and an inorganic acid (such as 36% HCl, or 2 mol/L $H_2SO_4$);
e) washing the product with 70-90% ethanol aqueous solution (V/V) until the amount of halide ion is less than 1%; and
f) dehydrating and drying (if required, freezing the product with liquid nitrogen and crushing into powders using a crusher).

The water-soluble hydroxyethylcellulose containing no carbonyl group may be, for example, prepared by the following processes:
a) immersing the cellulose into an about 18% NaOH solution in an organic solvent (such as acetone, isopropanol, or tert-butyl alcohol) at about 20-30° C. and alkalizing for 1-2 hours;
b) adding ethylene oxide having a weight 1-1.5 times of the weight of the raw materials and allowing to react at 70-90° C. for 1-3 hours, neutralizing to pH 6-8 with an inorganic acid (such as glacial acetic acid);
c) washing the resulting product with 70-90% organic solvent (V/V) (such as acetone, or ethanol) aqueous solution; and
d) dehydrating and drying (if required, freezing the product with liquid nitrogen and crushing into powders using a crusher).

The water-soluble etherified cellulose material (II type) having a carbonyl content not greater than 2% and a degree of polymerization of 100-400 may be, for example, prepared by the following methods:
a) using regenerated cellulose fabrics, fibers, powders, non-woven cloths or sponges as raw materials;
b) putting said raw materials into a closed reactor and allowing to react in a 2-3 g/L soft water solution of active chlorine (bath ratio 1:15-30) at pH 9-10.5 and at room temperature with stirring for 30-90 minutes, discharging, and washing;
c) reacting in a 2-3 g/L of hydrogen peroxide hard water solution in the presence of 1-5 g/L of a stabilizer at pH 9-10.5 and a temperature of 80-100° C. with stirring for 50-60 minutes, washing with hot water.

The following steps are identical to steps b); c); d); e); and f) in type I reaction.

Notes: the order of the above steps b) and c) can be inverted; or the reaction can be carried out by feeding in sequence half of the amount of feed of b), whole amount of feed of c), and then the other half of amount of the feed of b).

The above reactions produce type II oxidized-etherified cellulose products. As regard to a carboxymethylcellulose sodium, it has a degree of substitution of 0.45-0.90 and a degree of polymerization of 100-400. As compared with type I products, $COO^-$ is incorporated into the molecule of type II products upon oxidation and etherification. As a result, not only the hemostatic effect of the materials is improved, but also the materials are easily degraded from high molecular polysaccharides to low molecular polysaccharides in vivo so as to be absorbed by the organism The type I etherified celluloses of the invention can be used as external materials, and can be used for the hemostasis of a wound surface relating to nose, stomatology, gynaecology, haemorrhoids, and surgery. They may be prepared into fabrics, fibers, powders, capsules, sponges, films or colloidal liquid, and can be prepared, in combination with other materials, into band aids, transfusion bandages, autobinders, aerosols, first-aid kits and operation kits. They also have notable effect on patients suffering from blood coagulation disorders.

The type II oxidized-etherified cellulose products of the invention are useful for internal or external applications, and can be used for the operation hemostasis relative to neurosurgery, stomatology, nose, abdominal surgery, chest surgery, digestive tract, arthopedis, gynaecology, and haemorrhoids. They can be absorbed by a human body, and can be prepared into fabrics, fibers, powders, capsules, sponges, films or colloidal liquids, and aerosols. They may be spherical, columnar and suppository, and form, together with other operation tools, operation hemostatic clog. They also have notable effect on patients suffering from blood coagulation disorders.

In addition, when the etherified cellulose products of the invention are made into aerosols, firstly the etherified cellulose products are prepared into powders having a particle size below 300 mesh via spray drying, freeze drying, pneumatic crushing or direct crushing. Then the resulting powders are made into aerosols together with a propellant such as compressed nitrogen, carbon dioxide gas, freon, LPG or dimethyl ether, or together with surfactants or drugs. Alternatively, the prepared powders are directly sprayed onto a wound surface by the use of an electric or hand-air pump for hemostasis, absorption of exudates, inflammation, or protection of the wound surface, and prevention of adhesion.

The products of the invention can also be used in combination with some functional materials (such as biological growth factor, inflammatory, antibacterial, healing-promoting drugs), and made into functional medical materials or absorbable pharmaceutical carriers.

Furthermore, the I type and II type cellulose products of the invention can also be prepared into human body color pastes in combination with suitable components. For instance, the human body color pastes can be prepared by color printing (such as screen printing or ink-jet printing) colorful figures onto the materials made of the cellulose of the invention in the forms of fabrics, non-woven cloths or films. Due to the isolating action of the materials of the invention, the direct contact of ink with human body is avoided so that the stimulation to skin is avoided.

The etherified cellulose products of the invention can also be used in combination with various active ingredients, and made into skin-care masks. The cellulose products of the invention can also be made into water-soluble packaging materials, or various packaging materials for dust products, or used for insulation packaging of various materials that are prone to reactions, thereby allowing the materials to mix and react in water during use.

The fibrous cellulose product according to the present invention can be mixed with various fibers and dissolved in water in the subsequent steps in order to improve the degree of fineness of the yarns.

In addition, if needed, the cellulose product according to the present invention can be formed into a sheet, a colloid or an aerosol. The resultant product can be placed in the wound surface after an operation for the purpose of prevention of operation-adhesion. The product according to the present invention has excellent bio-absorbency and can be almost completely absorbed in vivo after a period of time.

The hemostatic effect and the absorption in vivo of the cellulose derivatives of the invention are described in experimental examples 1-4.

The cellulose derivatives of the invention have special effect on the hemostasis of patients suffering from blood coagulation disorders. A rabbit is injected with blood anticoagulant heparin to make the whole-body blood anticoagulative. Then a blood surface is made, and hemostatic respectively with soluble carboxymethylcellulose sodium and gelatin sponge. Bleeding time and bleeding amount are observed. The results show that there is no substantial difference in the bleeding time and the bleeding amount before and after anticoagulation in relation to carboxymethylcellulose sodium, while there is substantial difference in relation to the gelatin sponge.

Ellis H and Weibel M A M A Majno G pointed out respectively in *British Surgery Journal,* 69:241-243, 1982 and *American Surgery Journal,* 126:345-353, 1973, that, adhesion may occur in relation to 90% of operations due to the formation of scar tissues after an operation, 10% of which may cause postoperative problems. For instance, the adhesion related to uterine tube may cause sterility, the adhesion related to intestine may cause intestinal obstruction, and twice thoracotomy is necessary for the adhesion related to cardiac thorax. The water-soluble cellulose material of the invention can be dissolved and form gels, which is placed between tissues of different wound surfaces and can cover organs and tissues. Thus it can play a role of separation and lubrication effectively, thereby preventing different tissues of wound surfaces from contacting each other and adhering.

EXAMPLES

Example 1

20 g of absorbent cotton was added to a closed reactor, 300 mL of 50% NaOH (w/w) aqueous solution was added to the reactor, and the system was allowed to react at room temperature for 2 hours with stirring. Then 50 mL of 50% chloroacetic acid solution in ethanol (w/w) was added to the reactor and the system was allowed to continuously react for 8 hours. The resulting product was neutralized with 36% HCl to pH 6-8 and washed with an ethanol solution having an ethanol content above 75% until the amount of $Cl^-$ was less than 1% to give carboxymethylcellulose sodium (CMC-Na) [I] fiber, which has a degree of substitution of 0.4-0.5 and a degree of polymerization greater than 400. The product is slow-dissolving and anti-adhesion.

Example 2

20 g of absorbent cotton was added to a closed reactor, 50 mL of 50% chloroacetic acid solution in ethanol (w/w) was added to the reactor, and the system was allowed to react at room temperature for 1-2 hours with stirring, then 300 mL of 50% NaOH aqueous solution (w/w) was added to the reactor and the system was allowed to continuously react for 8 hours. The resulting product was neutralized with 36% HCl to pH 6-8 and washed with ethanol solution having an ethanol content above 75% until the amount of Cl was less than 1% to give carboxymethylcellulose sodium (CMC-Na) [I] fiber, which has a degree of substitution of 0.4-0.5 and a degree of polymerization greater than 400. The product is slow-dissolving and anti-adhesion.

Example 3

40 g of absorbent gauze was added to a closed reactor, 90 mL of 40-50% NaOH aqueous solution (w/w) and 200 mL of 95% ethanol (v/v) were added to the reactor, and the system was allowed to react at 20-30° C. for 3 hours with stirring. Then 100 mL of 30-70% chloroacetic acid solution in ethanol (w/w) was added to the reactor and the system was allowed to continuously react for 8 hours. The resulting product was neutralized with 36% HCl (w/w) to pH 6-8 and washed with an ethanol solution having an ethanol content above 75% until the amount of $Cl^-$ was less than 1% to give type I carboxymethylcellulose sodium (CMC-Na) gauze, which has a degree of substitution of 0.40-0.55 and a degree of polymerization greater than 400.

Example 4

40 g of absorbent gauze was added to a closed reactor, 100 mL of 30-70% chloroacetic acid solution in ethanol (w/w) was added to the reactor, and the system was allowed to react at 20-30° C. for 3 hours with stirring, then 90 mL of 40-50% NaOH aqueous solution (w/w) and 95% ethanol (v/v) 200 mL were added to the reactor and the system was allowed to continuously react for 8 hours. The resulting product was neutralized with 36% HCl (w/w) to pH 6-8 and washed with an ethanol solution having an ethanol content greater than 75% until the amount of Cl was less than 1% to give type I carboxymethylcellulose sodium (CMC-Na) gauze, which has a degree of substitution of 0.40-0.55 and a degree of polymerization greater than 400.

Example 5

100 parts of crushed cellulose was alkalized in 50% NaOH solution at 30° C. for 1 hour and the alkalized cellulose was added to an autoclave. 600 parts of liquid chloromethane was added to the autoclave and the system was allowed to etherify at $5.7 \times 10^5$ Pa and 75° C. for 13 hours. Chloroethane was recovered from the etherified product. The product was flocculated and purified with hot water at 80-90° C., neutralized with glacial acetic acid, washed twice with hot water, centrifugally separated, and dried (140° C.) to give methylcellulose powder having a degree of substitution of 1.8 and a degree of polymerization greater than 400.

Example 6

10 g of absorbent gauze was added to a closed reactor, and 30-50 mL of 25-50% NaOH aqueous solution (w/w) and 100-170 mL of 95% ethanol (v/v) were added to the reactor and the system was allowed to react at 20-30° C. for 1 hour with stirring. Then 50-90 mL of 30-70% chloroacetic acid solution in ethanol (w/w) was added to the reactor and the system was allowed to continuously react at 20-75° C. for 1.5-3 hours. The resulting product was neutralized with 36% HCl (w/w) to pH 6-8 and washed with an ethanol solution having an ethanol content above 75% until the amount of $Cl^-$ was less than 1% to give type I carboxymethylcellulose sodium (CMC-Na) gauze, which has a degree of substitution of 0.6-0.8 and a degree of polymerization greater than 400.

Example 7

50 g of a viscose fabric was placed into a reactor. 1,000 mL of 2 g/L sodium hypochlorite was added to the reactor. The pH was adjusted to 9-10.5. The materials were allowed to react at room temperature for 0.5-2 hours, discharged, and washed with water, then the pH was adjusted to 9.5-10.5. 2-4 g of a stabilizer (such as sodium silicate, sodium pyrophosphate or commercial hydrogen peroxide) and 1,000 mL of 25-30% hydrogen peroxide aqueous solution were added and the system was allowed to react at 85-100° C. with stirring for 1-2 hours. The resulting product was washed with hot water having a temperature greater than 85° C. for three times.

80-120 mL of 40-50% NaOH aqueous solution (w/w) and 280-320 mL of 95% ethanol (v/v) were added to the reactor and the system was allowed to react at 20-30° C. with stirring for 1-2 hours. Then 150-200 mL of 30-70% chloroacetic acid solution in ethanol (w/w) was added to the reactor and the system was allowed to continuously react at 20-75° C. for 1.5-5 hours. The resulting product was neutralized with 36% HCl (w/w) to pH 6-8 and washed with an ethanol solution having an ethanol content above 75% until the amount of $Cl^-$ was less than 1%. The resultant product was dehydrated, dried, packaged and sterilized to give type II oxidized carboxymethylcellulose sodium fabric capable of being absorbed in vivo, which has a degree of substitution of 0.65-0.90 and a degree of polymerization less than 400.

Example 8

50 g of a viscose fabric was placed into a reactor, 1,000 mL of 2 g/L sodium hypochlorite was added to the reactor, pH was adjusted to 9-10.5, the materials were allowed to react at room temperature for 0.5-2 hours, drained, and washed with water, then the pH was adjusted to 9.5-10.5. 2-4 g of a stabilizer (such as sodium silicate, sodium pyrophosphate or commercial hydrogen peroxide) and 1,000 mL of 25-30% hydrogen peroxide aqueous solution were added and the system was allowed to react at 85-100° C. with stirring for 1-2 hours, the resulting product was washed with hot water of greater than 85° C. for three times.

150-200 mL of 30-70% chloroacetic acid solution in ethanol (w/w) was added to the reactor and the system was allowed to react at 20-30° C. with stirring for 1-2 hours, then 80-120 mL of 40-50% NaOH (w/w) aqueous solution and 280-320 mL of 95% (v/v) ethanol were added to the reactor and the system was allowed to continuously react at 20-75° C. for 1.5-5 hours. The resulting product was neutralized with 36% HCl (w/w) to pH 6-8 and washed with an ethanol solution having an ethanol content greater than 75% until the amount of $Cl^-$ was less than 1%, dehydrated, dried, packaged and sterilized to give type II oxidized carboxymethylcellulose sodium fabric capable of being absorbed in vivo, which has a degree of substitution of 0.65-0.90 and a degree of polymerization less than 400.

Example 9

50 g of a viscose fabric was placed into a reactor, 1,000 mL of 2 g/L sodium hypochlorite was added to the reactor, pH was adjusted to 9-10.5, the materials were allowed to react at room temperature for 0.5-2 hours, drained, and washed with water, then the pH was adjusted to 9.5-10.5. 2-4 g of a stabilizer (such as sodium silicate, sodium pyrophosphate or commercial hydrogen peroxide) and 1,000 mL of 25-30% hydrogen peroxide aqueous solution were added and the system was allowed to react at 85-100° C. with stirring for 1-2 hours, the resulting product was washed with hot water of greater than 85° C. for three times.

40-60 mL of 40-50% NaOH (w/w) aqueous solution and 280-320 mL of 95% (v/v) ethanol were added to the reactor and the system was allowed to react at 20-30° C. with stirring for 1-2 hours, then 150-200 mL of 30-70% chloroacetic acid solution in ethanol (w/w) was added to the reactor and the system was allowed to continuously react at 20-75° C. for 1 hour. 40-60 mL of 40-50% NaOH (w/w) aqueous solution was further added. The system was allowed to continuously react at 20-75° C. for 1-2 hours. The resulting product was neutralized with 36% HCl (w/w) to pH 6-8 and washed with an ethanol solution having an ethanol content greater than 75% until the amount of $Cl^-$ was less than 1%, dehydrated, dried, packaged and sterilized to give type II oxidized carboxymethylcellulose sodium fabric capable of being absorbed in vivo, which has a degree of substitution of 0.65-0.90 and a degree of polymerization less than 400.

Example 10

Procedures and process conditions are identical to those described in Example 5, except that 200-300 g of viscose non-woven cloth was used as the raw material. A slow-dissolving and absorbable oxidized carboxymethylcellulose sodium [II] fabric was obtained.

Example 11

Procedures and process conditions are identical to those described in Example 5, except that viscose non-woven cloth was used as the raw material, 20 mL of 20-30% NaOH aqueous solution was used in the alkalization, and 70-120 mL of a solution of 95% ethanol (v/v):50% acetone(v/v)=1:1 was used. A type II oxidized carboxymethylcellulose sodium non-woven cloth was obtained, which has a degree of substitution of 0.40-0.8, and a degree of polymerization less than 400.

Example 12

25 g of a viscose fiber was placed into a reactor, 1,000 ml of 2 g/L sodium hypochlorite was added to the reactor, and the pH was adjusted to 9-10.5. The materials were allowed to react at room temperature for 0.5-2 hours, discharged, and washed with water, then the pH was adjusted to 9.5-10.5. 2-4 g of a stabilizer (such as sodium silicate, sodium pyrophosphate or commercial hydrogen peroxide) and 1,000 mL of 25-30% hydrogen peroxide aqueous solution were added and the system was allowed to react at 85-100° C. with stirring for 1-2 hours. The resulting product was washed with hot water having a temperature greater than 85° C. for three times.

100-150 mL of 40-50% NaOH aqueous solution (w/w) and 200-300 mL of 95% ethanol (v/v) were added and the system was allowed to react at 20-30° C. with stirring for 1-2 hours. Then 150-200 mL of 30-70% chloroacetic acid solution in ethanol (w/w) was added and the system was allowed to continuously react at 40-75° C. for 3-5 hours. The resulting product was neutralized with 36% HCl (w/w) to pH 6-8 and washed with an ethanol solution having an ethanol content above 75% until the amount of $Cl^-$ was less than 1%. The resulting product was dehydrated, dried, packaged and sterilized to give type II oxidized carboxymethylcellulose sodium fiber, which has a degree of substitution of 0.65-0.90 and a degree of polymerization less than 400. The fiber obtained was fluffy, soft, and easy to carding and processing.

Example 13

4 g of carboxymethylcellulose sodium having a degree of substitution of 0.6-0.7 was dissolved in 200 mL of distilled water, and the resulting solution was frozen in the tray of a refrigerating machine. After being frozen completely, the resulting material was lyophilized at 10-15° C. and a low pressure for 20-30 hours by using a vacuum pump to give a soft water-soluble spongy hemostatic material.

Example 14

4 g of oxidized carboxymethylcellulose sodium having a degree of substitution of 0.6-0.7 and a degree of polymerization less than 400 was dissolved in 200 mL distilled water. 1 g of tissue growth factor was added to the resulting solution and dissolved. Then as in Example 8, a sponge capable of hemostatic absorption and promoting wound healing was obtained.

Example 15

An oxidized-carboxymethylcellulose sodium fabric having a degree of substitution of 0.45 and a degree of polymerization less than 400 was coated with a 2-10% polysaccharide solution and combined with absorbable alginic acid or chitosamine non-woven cloth to give an absorbable anti-adhesion hemostatic material.

Experimental Example 1

Thrombase Time Experiment

The material was prepared into 1% aqueous solution, then thrombase time (TT) was measured by using an auto-coagulation apparatus DATE AUTOFZ (U.S.A).

1. The results of the effects of the water-soluble carboxymethylcellulose sodium, oxidized-carboxymethylcellulose sodium, methylcellulose, ethylcellulose and hydroxyethylcellulose according to the invention, and water-insoluble oxidized cellulose, traditional gelatin sponge, and hemostatic fiber on TT were shown in Table 1.

TABLE 1

Effects of water-soluble materials and water-insoluble materials on TT ($P < 0.001$)

| Materials | TT (seconds) |
|---|---|
| Blank | 15.48 ± 0.74 |
| Carboxymethylcellulose sodium, degree of substitution 0.55 | 11.22 ± 0.35*** |
| Oxidized carboxymethylcellulose sodium, degree of substitution 0.62 | 11.78 ± 0.57*** |
| Methylcellulose, degree of substitution 1.8 | 11.22 ± 0.35 |
| Ethylcellulose, degree of substitution 1.2 | 13.57 ± 0.7 |
| Hydroxyethylcellulose, degree of substitution 0.9 | 13.78 ± 0.48 |
| Water-insoluble oxidized cellulose | 14.48 ± 1.14 |
| Gelatin sponge | 14.66 ± 0.48 |
| Hemostatic fiber (polyvinyl alcohol) | 14.78 ± 0.74 |

It can be seen from Table 1 that water-soluble carboxymethylcellulose sodium, oxidized carboxymethylcellulose sodium, methyl cellulose, ethyl cellulose and hydroxyethyl cellulose can substantially shorten TT and are superior to hemostatic materials such as water-insoluble oxidized cellulose, gelatin sponge and poly(vinyl alcohol).

2. The effects of the degrees of substitution on the hemostatic property were shown in Table 2.

TABLE 2

Effects of the degree of substitution of carboxymethylcellulose sodium water-soluble hemostatic materials on TT

| Degree of substitution | TT (seconds) |
|---|---|
| 0.49 | 11.6 ± 0.6*** |
| 0.68 | 11.9 ± 0.8*** |
| 0.82 | 12.7 ± 0.3* |
| 0.95 | 14.5 ± 0.8 |
| 1.2 | 14.8 ± 0.5 |
| 1.5 | 15.4 ± 0.8 |
| Blank | 15.5 ± 0.7 | n = 6,
***$P < 0.0001$,
*$P < 0.05$

It can be seen from Table 2 that TT was gradually shortened with the decrease of the degree of substitution. When the degree of substitution was greater than 0.9, the hemostatic effect was attenuated; when the degree of substitution was 1.0-1.2, the hemostatic effect still remained; and when the degree of substitution was above 1.5, the hemostatic effect vanished.

3. In order to further study the effect of solubility on the hemostatic property, in the invention, following comparison was made. Soluble materials were treated by using H+ to replace alkali metal ions so as to close the water-soluble groups and become insoluble materials, which were then compared with the original soluble materials having completely identical structures in relation to their hemostatic property. The results were shown as follows:

TABLE 3

Comparison of thrombinogen time of water-soluble materials and corresponding water-insoluble materials

| Materials | Water-soluble (TT seconds)-Na salt | Water-insoluble TT seconds) -H |
|---|---|---|
| Carboxymethylcellulose [I] type | 11.78 ± 0.57 | 12.36 ± 1.38 |
| Oxidized carboxymethylcellulose [II] | 12.61 ± 0.63 | 14.49 ± 1.46* |
| Blank | | 15.23 | n = 8
$P < 0.05$
*means substantial significance

Table 3 showed that both water-soluble materials and corresponding water-insoluble materials have hemostatic effect, but water-soluble materials exhibit better hemostatic property than corresponding water-insoluble materials.

Experimental Example 2

Effects of water-soluble materials and water-insoluble materials on blood viscosity:

The increase of blood viscosity is advantageous to blood coagulation. One of the unique advantages of water-soluble materials lies in that they can affect the viscosity of blood.

Three different hemostatic materials, water-soluble materials, water-insoluble oxidized cellulose and alginic acid, at the same amounts were respectively added to the blood, which had been anticoagulation-treated. The change in viscosity of the blood was observed. The results showed that the water-insoluble hemostatic materials had no effect on the viscosity of blood and the water-soluble hemostatic materials increased the viscosity of blood greatly. The results were shown in Table 4.

TABLE 4

Effects of water-soluble materials and water-insoluble materials on blood rheology in vitro

| Group | Whole blood viscosity (mPa.s) | | | Convergence |
| | $2\ second^{-1}$ | $47\ second^{-1}$ | $118\ second^{-1}$ | index |
|---|---|---|---|---|
| Control | 8.36 ± 1.17 | 4.24 ± 0.28 | 3.57 ± 0.21 | 2.33 ± 0.21 |
| Oxidized carboxymethylcellulose sodium [II] | 10.3 ± 1.22* | 5.35 ± 0.09** | 4.49 ± 0.06** | 2.29 ± 0.29 |
| Water-insoluble oxidizied cellulose | 9.73 ± 1.21 | 4.48 ± 0.12 | 3.7 ± 0.11 | 2.63 ± 0.3 |
| Control | 7.36 ± 0.85 | 3.83 ± 0.18 | 3.25 ± 0.11 | 2.27 ± 0.26 |
| Carboxymethylcellulose sodium [I] | 16.7 ± 3.01** | 6.55 ± 0.50** | 5.42 ± 0.38** | 2.77 ± 0.38 |
| Alginic acid | 9.21 ± 1.35* | 3.96 ± 0.28 | 3.32 ± 0.18 | 3.08 ± 0.45* |

Notes
*means compared with control, p < 0.05;
**means compared with control, P < 0.001; n = 5

The experiments of in vitro blood rheology showed that both water-soluble oxidized carboxymethylcellulose sodium and carboxymethylcellulose sodium substantially increased the whole blood viscosity at different shear rates. Water-insoluble oxidized cellulose basically had no effect on the whole blood viscosity at different shear rates. Although alginic acid materials may increase the whole blood viscosity at low shear rates and the convergence index, the effect of water-insoluble materials was obviously inferior to that of water-soluble materials.

Experimental Example 3

Effects of water-soluble materials and water-insoluble materials on the formation of thrombus:

Three different hemostatic materials, water-soluble materials, oxidized cellulose, and alginic acid, were added to an in vitro thrombus test apparatus. The formation of in vitro thrombus was observed. The results showed that the length and weight of thrombus of water-soluble hemostatic materials were obviously better Man those of other materials.

TABLE 5

Comparison of formation of in vitro thrombus of water-soluble materials and water-insoluble materials

| Material name | Wet weight of thrombus (mg) | Wet length of thrombus (cm) | Dry weight of thrombus (mg) | Dry length of thrombus (cm) |
|---|---|---|---|---|
| Carboxymethylcellulose sodium [I] type | 148.38 ± 18.58 | 4.67 ± 2.02 | 26.8 ± 5.07 | 3.7 ± 1.91 |
| Oxidized carboxymethylcellulose sodium [II] type | 34.33 ± 6.92 | 1.03 ± 0.15 | 5.62 ± 0.15 | 0.93 ± 0.15 |
| Alginic acid | 3.18 ± 0.51 | 0.07 ± 0.12 | 0.5 ± 0.87 | 0.07 ± 0.12 |
| Water-insoluble oxidized cellulose | No thrombus | No thrombus | No thrombus | No thrombus |
| Blank control | No thrombus | No thrombus | No thrombus | No thrombus |

Table 5 showed that, as regard to the anticoagulation-treated blood, under the rheology conditions, the formation of thrombus occurs in relation to the water-soluble hemostatic materials. The water-insoluble alginic acid materials exhibited a slight effect with respect to the formation of thrombus, while the water-insoluble oxidized cellulose and control materials had no coagulation effect.

Experimental Example 4

The absorption and metabolism of the type II water-soluble hemostatic materials according to the invention:

Oxidized carboxymethylcellulose sodium and other hemostatic materials were implanted into an animal body together. The animal was killed at specified time, and its liver, kidney, bone, brain, and lung were taken and prepared into pathological sections. Material residue, inflammatory reaction and formation of foreign matter giant cell and fiber parent cell were observed. The results showed that gauze residue was invisible to the naked eye one week after the operation, the residue in pathological sections disappeared four weeks after the operation and was completely absorbed 90 days after the operation. The reaction of tissues was very slight. As compared with the control, it exhibited more rapid absorption rate and less reaction.

The amounts of the gauze in blood, liver, and kidney of a rat were quantitatively measured respectively 1 hour, 3 days, 7 days, 14 days, and 30 days after the water-soluble hemostatic material was injected into the abdominal cavity of the rat. The change in the molecular weight of the material was simultaneously measured. The results showed that the molecular weight of the material was reduced to 40-50% after 30 days. Most of the material was excreted from the body via the circulating system of the rat, a small part of the material remained in liver and was absorbed upon decomposition by phagocyte. Indexes including Blood routine, urine routine and body temperature of the rat were examined at regular intervals after the operation. The results showed that there is no substantial difference in the indexes as compared with normal wound reactions. This showed tat even though a small amount of the material remained in the liver, organic changes may not occur.

The material was imbedded in abdominal cavity of a rat, and the change in the blood viscosity of the rat before and after imbedding was examined. The results showed that no notable differences were found. Therefore, thrombus will not form in blood vessels.

$^3$H-glycine isotope was used to mark oxidized-carboxymethylcellulose sodium injected into the abdominal cavity of a rat. The distribution and metabolism of the material in organs were observed. The distribution and metabolism of the material in spleen, kidney, liver, excrement, urine, large intestine, duodenum, lung, abdominal cell, peritoneal effusion, blood and gallbladder were respectively observed 1 hour, 3.5 hours, 7 hours, 1 day, 7 days, 14 days, 21 days, 28 days, 42 days and 56 days after the operation. The results showed that, 31.8% of the material entered into the urine, and 4.1% of the material entered into the blood 1 hour after the operation. 14.9% of the material entered into the excrement, and 10.8% of the material entered into the urine 3.5 hours after the operation. 7 hours after the operation, above 94% of the material was excreted out of the body via the blood, excrement and urine. After 21 days, 98% of the material was excreted out of the body, and only 2.2% of the material remained in the body, 1.6% of which remained in the liver, but did not cause organic changes.

Comparative Experimental Example 4

Six healthy rabbits having a body weight of about 2.5 kg were divided into 3 groups, 2 in each group, anaesthetized with a 3% pentobarbital solution. Two sides of the spinal column were cut according to surgery operation requirements. Water-soluble materials having a degree of polymerization greater than 400 were imbedded into the muscle of each of the rabbits at three sites. Then all the cuts were sutured The muscular tissues (including the hemostatic gauze imbedded) in the imbedding parts were taken out 7, 14 and 90 days, respectively, after the operation, fixed with a formaldehyde solution, dyed with TH, and made into pathological sections. The results of observations were shown in Table 6.

TABLE 6

Tissue reactions of carboxymethylcellulose sodium water-soluble materials having a high degree of polymerization

| Imbedding days | 7 days | 14 days | 90 days |
|---|---|---|---|
| Gauze sectional area (cm$^2$) | 0.8 × 0.5 | 0.4 × 0.3 | 0 |
| Inflammatory reaction | +-++ | ++-+++ | ++-++++ |
| Fiber proliferation | +-++ | ++-+++ | ++-+++ |
| formation of Liquefied cavity | Yes | Yes | 0 |

It can be seen from Table 6 that, after water-soluble materials having a degree of polymerization greater than 400 were imbedded into the body, inflammatory reaction and fiber proliferation increased with the time, and liquefied cavity was formed.

Above preparation examples and experimental examples are only illustrative, not limiting the scope of the invention defined by claims.

The invention claimed is:

1. A process for preparing medical and treatment products, comprising:
   (i) providing at least one oxidized-etherified cellulose derivative selected from the group consisting of water-soluble methylcellulose, ethylcellulose, hydroxyethylcellulose and salts of carboxymethylcellulose having a degree of substitution of 0.4-2.6, an average degree of polymerization of 100 to 1500 and a carbonyl amount greater than 0 and below 2%; and
   (ii) forming the oxidized-etherified cellulose derivative into the medical and treatment products.

2. The process according to claim 1, wherein said oxidized-etherified cellulose derivative is selected from the group consisting of water-soluble inethylcellulose, ethylcellulose, hydroxyethylcellulose and salts of carboxymethylcellulose having a degree of substitution of 0.4-2.6, an average degree of polymerization of 100 to 400 and a carbonyl amount greater than 0 and below 2%.

3. The process according to claim 2, wherein said oxidized-etherified cellulose derivative is selected from the group consisting of methylcellulose having a degree of substitution of 1.3-2.6, ethylcellulose having a degree of substitution of 1.0-1.5, hydroxyethylcellulose having a degree of substitution of 0.8-2.5 and salts of carboxymethylcellulose having a degree of substitution of 0.4-0.9.

4. The process according to claim 2, wherein said oxidized-etherified cellulose derivative has a pH value of 6 to 8.

5. The process according to claim 2, wherein said oxidized-etherified cellulose derivative is selected from the group consisting of methylcellulose having a degree of substitution of 1.5-2.2, ethylcellulose having a degree of substitution of 1.1-1.4, hydroxyethylcellulose having a degree of substitution of 1.0-2.0 and salts of carboxymethylcellulose having a degree of substitution of 0.45-0.9.

6. The process according to claim 2, wherein said oxidized-etherified cellulose is selected from the group consisting of methylcellulose having a degree of substitution of 1.8-2.0, ethylcellulose having a degree of substitution of 1.2-1.3, hydroxyethylcellulose having a degree of substitution of 1.5-1.8 and salts of carboxymethylcellulose having a degree of substitution of 0.5-0.85.

7. The process according to claim 2, wherein said salts are sodium salts, potassium salts, calcium salts, magnesium salts or aluminum salts.

8. The process according to claim 2, wherein said medical and treatment products are in a form of powders, fibers, webs, nonwoven cloths, sponges, films, capsules, pellets, columns, plugs or colloids.

9. The process according to claim 2, wherein said medical and treatment products include band aids, transfusion bandage, first-aid kit, operation kit, aerosols, color bandage for human body, skin care masks, packaging materials, water-soluble decrement mixed yam, or cloths.

10. Water-soluble oxidized-etherified cellulose selected from the group consisting of methylcellulose, ethylcellulose, hydroxymethylcellulose and salts of carboxymethylcellulose having an average degree of polymerization of 100 to 1500, a carbonyl amount above 0% and below 2% and a degree of substitution of 0.4 to 2.6.

11. The water-soluble oxidized-etherified cellulose according to claim 10, having an average degree of polymerization of 100-350.

12. The water-soluble oxidized-etherified cellulose according to claim 11, having an average degree of polymerization of 150-350.

13. The water-soluble oxidized-etherified cellulose according to claim 12, having an average degree of polymerization of 150-300.

14. The water-soluble oxidized-etherified cellulose according to claim 10, having a carbonyl amount in a range of from 0.001 to below 2%.

15. The water-soluble oxidized-etherified cellulose according to claim 10, which is a salt of water-soluble carboxymethylcellulose.

16. The water-soluble oxidized-etherified cellulose according to claim 15, which is a salt of water-soluble carboxymethylcellulose having a degree of substitution of 0.4-0.9 and an average degree of polymerization of 100 to 400.

17. The water-soluble oxidized-etherified cellulose according to claim 10, wherein said salts are selected from the group consisting of sodium salts, potassium salts, calcium salts, magnesium salts and aluminum salts.

18. The water-soluble oxidized-etherified cellulose according to claim 10, wherein said water-soluble oxidized-etherified cellulose contains 0.01 to 2wt % of $Ca^{2+}$ after an impregnation treatment.

19. A preparation process of the water-soluble oxidized-etherified cellulose as claimed in claim 10, comprising
   (i) treating a natural or regenerated cellulose with an oxidant to give an oxidized cellulose;
   (ii) treating the oxidized cellulose with a medium containing an alkali metal hydroxide;
   (iii) adding a solution of an alkyl halide or a halogenated acetic acid in a C1-C5 lower alkanol into the system of (ii) to effect an etherification reaction;
   (iv) neutralizing the system from (iii) with a solution of a C1-C5 lower alkanol and an inorganic acid until the pH value of the system reaches 6-8; and washing and drying,
   wherein said step (iii) can be carried out before said step (ii), and said step (ii) and/or step (iii) can be carried out as many times as required.

20. Medical and treatment products comprising said water-soluble oxidized-etherified cellulose as claimed in any one of claims 10-17.

21. The medical and treatment products according to claim 20, which are in the form of powders, fibers, fabrics, non-woven fabrics, sponges, films, capsules, pellets, columns, plugs or colloids.

22. The water-soluble oxidized-etherified cellulose according to claim 10, having an average degree of polymerization of 100-400.

* * * * *